United States Patent [19]

Somasekhara et al.

[11] 3,985,761

[45] Oct. 12, 1976

[54] NITROTHIAZOLYL DERIVATIVES OF NITROSTYRENE

[75] Inventors: Shankar Somasekhara; Dinesh Maganlal Desai; Navinchandra Vasantrai Upadhyaya, all of Baroda, India

[73] Assignee: Sarabhai Research Centre, Baroda, India

[22] Filed: Oct. 24, 1974

[21] Appl. No.: 517,685

[52] U.S. Cl. .................. 260/302 R; 260/471 C; 260/622 R; 424/270
[51] Int. Cl.² .............................. C07D 277/34
[58] Field of Search .............................. 260/302 R

[56] References Cited
OTHER PUBLICATIONS

Koremura et al., Chem. Abstracts, vol. 57, col. 16450c to col. 16451h (1962).

Schales et al., J.A.C.S., vol. 74, pp. 4486–4490, 1952.

*Primary Examiner*—Nicholas S. Rizzo
*Assistant Examiner*—D. B. Springer
*Attorney, Agent, or Firm*—Ladas, Parry, Von Gehr, Goldsmith & Deschamps

[57] ABSTRACT

Hydroxy substituted nitrostyrene derivatives have been found to exhibit antibacterial and anthelmintic properties. Derivatives having a nitrothiazolyloxy moiety have low toxicity and a broad spectrum antimicrobial activity.

4 Claims, No Drawings

NITROTHIAZOLYL DERIVATIVES OF NITROSTYRENE

BACKGROUND OF THE INVENTION

Compounds based on hydroxy substituted nitrostyrene have been developed as of special interest having antifungal, antibacterial and anthelmintic properties. Antimicrobials and anthelmintics were the subject of the investigations.

It is an object of this invention to prepare substituted hydroxynitrostyrene derivatives using an organic aldehyde to produce new compounds having properties not reported in the literature.

SYNOPSIS

The compounds of the present invention are prepared as follows:

Aromatic aldehydes of the general formula:

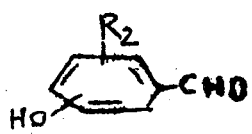
II wherein $R_2$ = H, Cl or Br are condensed with nitroalkanes of the general formula $R_1CH_2-NC_2$ wherein $R_1$ is H, $CH_3$ or $C_2H_5$ and the resultant β-nittestyrene derivatives of the general formula

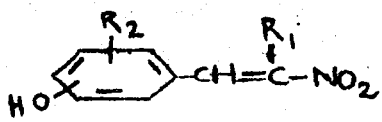
III wherein $R_1$ and $R_2$ have the same meaning as defined above, are, if desired, reacted with (i) a compound of formula $R_4-N=C=X$ where X is O or S, $R_4$ is $C_1-C_4$ alkyl, $C_5-C_6$ cycloalkyl, phenyl, chlorophenyl, bromophenyl, iodophenyl, anisyl, tolyl or nitrophenyl, or (ii) 5-nitro-2-chloro thiazole to obtain compounds of the general formula

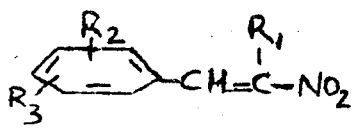
I wherein $R_1=H, CH_3$ or $C_2H_5$, $R_2=H, Cl$ or Br and $R_3$ is $-OCONHR_4$, $-OCSNHR_4$ or 5-nitrothiazol-2yl-oxy wherein $R_4$ is as defined earlier.

It is an object of this invention to propose new substituted hydroxynitrostyrene derivatives having antifungal, antibacterial and anthelmintic properties.

It is another object of this invention to propose new substituted hydroxynitrostyrene derivatives having antifungal, antimicrobial and anthelmintic properties which have low toxicity.

Yet another object of this invention is to propose a process for preparing the said compounds by an economical and uncomplicated process.

PRIOR ART

It is known from C.A. Vol. 62, p.p.14569e that 3-nitro-4-hydroxy-β-nitrostyrene has been claimed to have antifungal properties against plant pathogenic fungi.

It has not been reported in the art that hydroxy substituted nitrostyrene derivatives have any other property other than antifungal property.

It is also not known to prepare any other substituted hydroxynitrostyrene derivatives excepting a few earlier (J.Am.Chem. Soc, 74, 4486 (1952), and J. Org. Chem, 18, 1–3 (1953).

We have surprisingly found that some new compounds of substituted hydroxynitrostyrene derivatives have antibacterial as well as anthelmintic properties.

We have still further unexpectedly found that in general all the compounds discovered by us, have antimicrobial and anthelmintic properties. Further, we have discovered that by blocking the hydroxy group with a nitrothiazole moiety we can obtain products with low toxicity having a broad spectrum antimicrobial activity. Again we have been able to prepare new m-hydroxynitrostyrenes and their carbamate derivatives which are very active against cestodes (*Hymenolepis nana*). Further we have discovered that the activity of the nitrostyrene derivatives of our inventions can be enhanced by a β-methyl or a β-ethyl group.

DETAILED DESCRIPTION OF THE INVENTION

According to this invention there is provided a process for preparing substituted hydroxynitrostyrene derivatives of the formula

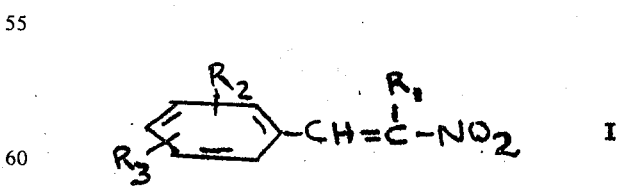
I wherein $R_1$ is H, $CH_3$ or $C_2H_5$, $R_2$ is H, Cl, or Br and $R_3$ is OH, or

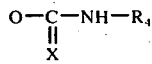

or 5-nitrothiazol-2-yl-oxy, wherein X is O or S and R₄ is C₁–C₄ alkyl, C₅–C₆ cycloalkyl, phenyl, chlorophenyl, bromophenyl, iodophenyl, anisyl, tolyl or nitrophenyl with the previso that when R₁ and R₂ are both H, R₃ is not 4—CH which comprises reacting a compound of formula

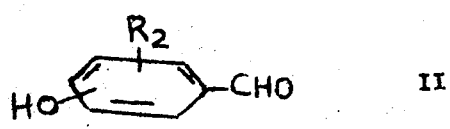

wherein R₂ is as defined before with a lower alkyl amine like propylamine or butylamine, in a hydrocarbon solvent medium at around reflux temperature of the solvent used to produce the corresponding aldimine, thereafter reacting the obtained aldimine product with a nitroalkane of the formula

wherein R₁ is as defined before, in an aliphatic acid medium or an alcoholic medium having an aliphatic acid at about 50° to 110° C to produce a compound of formula

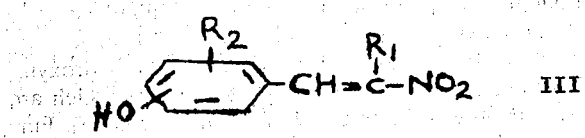

followed by, when desired, reacting the —OH group, through its alkalimetal salt, either formed in situ or isolated, (i) with a nitrothiazole or formula

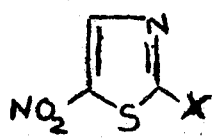

wherein X is a halogen like chloro or bromo to produce compounds of formula I wherein R₃ is 5-nitrothiazol-2-yl-oxy or (ii) with an isocyanate or or an isothiocyanate of the general formula R₄ — N=C=X wherein X is O or S and R₄ is as defined before to produce compounds of formula I wherein R₃ is

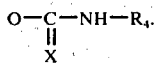

The first stage of the reaction, namely the production of the aldimine derivatives, can be carried out in either of the following ways:

The intermediate compound produced can be isolated and reacted separately at the subsequent stage or the hydrocarbon solvent can be removed from the reaction system after the first stage reaction and then the second stage reaction carried out using aliphatic acid medium or an alcoholic medium having an aliphatic acid. Thus the aliphatic acid can be employed both as a reaction medium and a catalyst or as a catalyst alone.

It is to be observed that the products conforming to the formula

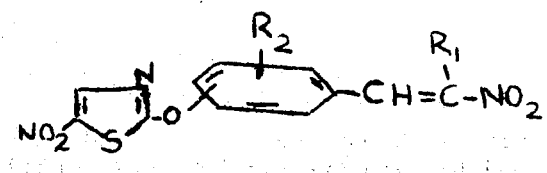

can also be produced using as starting material an organic aldehyde having the nitrothiazole substitution and it has also been found that this process is very uneconomical and of less commercial significance.

DETAILED INVESTIGATION OF THE PROPERTIES OF THE NEW COMPOUNDS

Antimicrobial properties have been studied by the serial dilution technique against the following organisms:

S.a. = Staph aureus, E.c. = E.coli, S.s. = S.Shigae, S.t. = S. typhi, P.a. = Ps.aeruginosa, Ca = Candia alibicans, T.m = Trichophton mentagrophytes, M.gy = Microsporum Gypseum, Ph. je = Phialophora jeanselmei, N.a. = Nocardia asteroides A.f = Aspergillus fumigatus, and antibiotic resistant Staph aureus.

The minimum inhibitory concentrations are expressed in micrograms per milliliter.

The data on some of the compounds studied are represented in Table I.

TABLE-I

ANTIMICROBIAL ACTIVITY OF NITROSTYRENE DERIVATIVES
(MIC Values in mcg/ml)

| COMPOUND FORMULA | S.a | A/R S.a | E.C. | S.s | S.t | Pr.ox | P.a |
|---|---|---|---|---|---|---|---|
| CH₃—⟨phenyl⟩—NHCOO—⟨phenyl⟩—CH=C(CH₃)—NO₂ | 6.25 | 6.25 | 6.25 | 12.5 | 50.0 | 6.25 | 50.0 |

TABLE-1-continued
ANTIMICROBIAL ACTIVITY OF NITROSTYRENE DERIVATIVES
(MIC Values in mcg/ml)

| Compound | | | | | | | |
|---|---|---|---|---|---|---|---|
| $B_\gamma$—C$_6$H$_4$—NHCOO—C$_6$H$_4$—CH=C(CH$_3$)—NO$_2$ | 6.25 | 12.5 | 6.25 | 6.25–12.5 | 50.0 | 6.25 | 50.0 |
| $C_4H_9$NHCOO—C$_6$H$_4$—CH=C(CH$_3$)—NO$_2$ | 6.25 | 6.25 | 6.25–12.50 | 12.5 | 50.0 | 6.25 | 50.0 |
| Cyclohexyl-NHCOO—C$_6$H$_4$—CH=C(CH$_3$)—NO$_2$ | 3.125 | 3.125 | 6.125–12.50 | 12.5 | 50.0 | 6.25–12.5 | 50.0 |
| C$_6$H$_5$—NHCOO—C$_6$H$_4$—CH=C(CH$_3$)—NO$_2$ | 6.25 | 3.125–6.25 | 6.25 | 6.25 | 50.0 | 12.5 | 50.0 |
| HO—C$_6$H$_4$—CH=C(CH$_3$)—NO$_2$ | 3.125 | 3.125 | 3.125 | 3.125 | 50.0 | 3.125 | 50.0 |
| (5-nitrothiazol-2-yl)-O—C$_6$H$_4$—CH=C(CH$_3$)—NO$_2$ | 1.56 | 1.56 | 3.125 | 3.125 | 50.0 | 1.56–3.125 | 50.0 |
| HO—(Cl)C$_6$H$_3$—CH=C(CH$_3$)—NO$_2$ | 3.125 | 3.125 | 12.5–25.0 | 25.0 | 50.0 | 6.25 | 50.0 |
| Cl—(OH)C$_6$H$_3$—CH=CH—NO$_2$ | 3.125 | 3.125 | 50.0 | 50.0 | 50.0 | 25.0 | 50.0 |
| $B_\gamma$—C$_6$H$_4$—NHCOO—(Cl)C$_6$H$_3$—CH=C(CH$_3$)—NO$_2$ | 6.25 | 6.25 | 50.0 | 25.0 | >50.0 | 6.25 | 50.0 |

| COMPOUND FORMULA | C.a | T.m | M.gy | Ph.je | N.a | A.f |
|---|---|---|---|---|---|---|
| CH$_3$—C$_6$H$_4$—NHCOO—C$_6$H$_4$—CH=C(CH$_3$)—NO$_2$ | 12.5 | 3.125 | 1.56–3.125 | 6.25 | 25.50 | 12.50 |
| $B_\gamma$—C$_6$H$_4$—NHCOO—C$_6$H$_4$—CH=C(CH$_3$)—NO$_2$ | 22.5–25.0 | 1.56 | 1.56 | 1.56 | 50.0 | 12.50 |
| $C_4H_9$NHCOO—C$_6$H$_4$—CH=C(CH$_3$)—NO$_2$ | 12.5–25.0 | 0.78 | 0.39–0.78 | 0.78 | 50.0 | 6.25 |
| Cyclohexyl-NHCOO—C$_6$H$_4$—CH=C(CH$_3$)—NO$_2$ | 25.0 | 0.78 | 6.25 | 6.25 | 50.0 | 6.25–12.50 |
| C$_6$H$_5$—NHCOO—C$_6$H$_4$—CH=C(CH$_3$)—NO$_2$ | 25.0 | 3.125–6.25 | 3.125 | 3.125 | 25.0 | 6.25 |
| HO—C$_6$H$_4$—CH=C(CH$_3$)—NO$_2$ | 12.5 | 1.56 | 1.56 | 3.125 | 25.0 | 6.25 |

TABLE-I-continued
ANTIMICROBIAL ACTIVITY OF NITROSTYRENE DERIVATIVES
(MIC Values in mcg/ml)

| Structure | | | | | | |
|---|---|---|---|---|---|---|
| 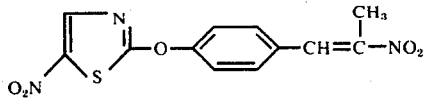 | 3.125 | 0.19 | 0.39–0.78 | 0.39 | 12.50 | 1.56 |
| 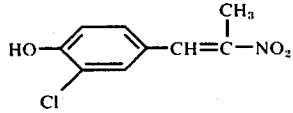 | 12.50 | 1.56 | 1.56 | 3.125 | 50.0 | 6.25 |
| 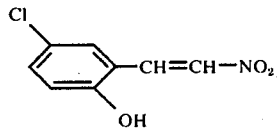 | 25.50 | 6.25 | 6.25–12.50 | 12.50 | 25.0 | 12.5<br>25.0 |
| 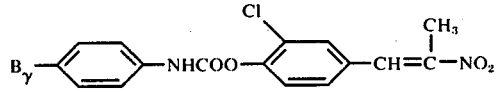 | 25.0 | 1.56 | 1.56 | 3.125 | 50.0 | 6.25 |

S.a = *Staph. aureus*, E.c. = *E.coli*, S.s = *S.Shigae*, S.t = *S. typhi*, P.a = *Ps. aeruginosa*, C.a = *Candida albicans*, T.m = *Trichophyton mentagrophytes* M.gy = *microsporum gypseum*, Ph.je=*Phialophora jeanselmei*, N.a = *Nocardia asteroides* A.f = *Aspergillus fumigatus* Pr.ox = *Proteus vulgaris* ox 19.

The anthelmintic properties of the products of the invention have been determined as follows:

Albimo mice of either sex (18–20 g.weight range) were administered by gavage 0.2 ml of the standard inoculum (containing 1000 viable eggs). 20 days later, the faecal matter was checked for *Hymenolipis nana* eggs. Mice showing the presence of *H nana* eggs were taken for experiments. They were classified on the weight basis. 5 animals were taken in each cage.

Compounds of the invention under investigation were suspended in 0.2% tragacanth. Concentrations were adjusted in such a way that 0.2 ml conformed to particular dosage schedule for each compound. They were administered by gavage in fasting condition in the morning on 21st day post infection, once daily for 3 consecutive days. For each set of test compound group, one cage of infected control mice was kept. These received saline for 3 days.

After 3 consecutive days of administration, all mice were kept fasting on the subsequent day (24th day post infection) and sacrificed on the 25th day. Results of surviving mice only have been taken. From each mouse, the whole intestine including caecum was collected in a petri dish with water. It was cut open longitudinally and was examined for adult worms and scolices. Absolute clearance of worms and scolices in individual mouse was taken as a criterion for assessing the results of each group.

The data on some of the compounds studied are represented in Table II

TABLE II
ACTIVITY AGAINST TAPEWORMS
Hymenolepsis nana in mice.

| Structure | Activity: % of infected mice getting 100% clearance | Dose mg/kg/ day × Number of days |
|---|---|---|
| 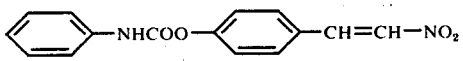 | 90 | 350 × 3 |
| 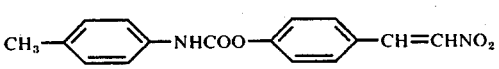 | 94 | 400 × 3 |
| 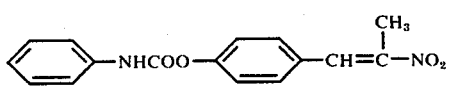 | 100 | 400 × 3 |
| 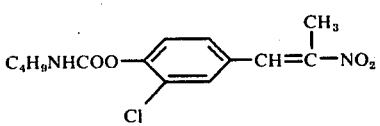 | 100 | 400 × 3 |
| 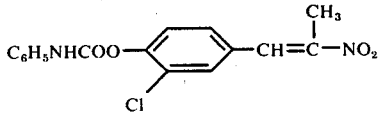 | 100 | 400 × 3 |

TABLE II-continued

ACTIVITY AGAINST TAPEWORMS
Hymenolepsis nana in mice.

| Structure | Activity: % of infected mice getting 100% clearance | Dose mg/kg/ day × Number of days |
|---|---|---|
| CH₃—⟨⟩—NHCOO—⟨⟩(Cl)—CH=C(CH₃)—NO₂ | 100 | 400 × 3 |
| Br—⟨⟩—NHCOO—⟨⟩—CH=CH—NO₂ | 100 | 400 × 3 |
| ⟨⟩—NHCOO—⟨⟩—CH=C(CH₃)—NO₂ | 100 | 400 × 3 |
| CH₃—⟨⟩—NHCOO—⟨⟩—CH=C(CH₃)—NO₂ | 100 | 200 × 3 |
| C₄H₉—NHCOO—⟨⟩—CH—C(CH₃)—NO₂ | 100 | 400 × 3 |

The following examples illustrate how some of the compounds of the invention can be prepared and is not to be construed as a limitation thereof.

EXAMPLE 1

β-Methyl-3-hydroxynitrostyrene 3-hydroxybenzaldehyde (12.2 g) and n-butylamine (9.12 g.) were refluxed in dry benzene (100 ml.) using Dean-Stark water separator for 3 hours. Benzene phase was concentrated. The residual solid, the crude aldimine, was filtered after cooling. The aldimine (17.5 g.) nitroethane (17.5 ml.) and glacial acetic acid (52 ml.) were heated for 30 minutes at 100° C. The reaction mixture was diluted with cold water. The crude title product thus obtained was crystallised from aqueous ethanol; m.p. 96°–98° C.

EXAMPLE 2

3-Bromo-4-hydroxynitrostyrene

3-Bromo-4-hydroxybenzaldehyde (20.1 g.) and n-propylamine (7.6 g.) were refluxed in dry benzene (150 ml.) using Dean-Stark water separator for 3 hours. Benzene phase was concentrated to get the crude aldimine as an oily product. The aldimine (24.2 g), nitromethane (24 ml.) and glacial acetic acid (72 ml.) were refluxed for 45 minutes. The reaction mixture was diluted with cold water. The solid was filtered off and crystallised from aqueous ethanol to obtain the title product; m.p. 132°–34° C.

EXAMPLE 3

β-Methyl-3-bromo-4-hydroxynitrostyrene

3-Bromo-4-hydroxybenzaldehyde (20.1 g.) and n-butylamine (9.12 g.) were refluxed in dry toluene (100 ml.) using Dean-Stark water separator for 4 hours. Organic phase was concentrated. The oily intermediate (25.6 g.), nitroethane (25.5 ml.) and propionic acid (77 ml.) were heated at 110° C for 1 hour. The reaction mixture was poured into crushed ice. The solid product was filtered off and crystallized from aqueous ethanol to obtain the title product, m.p. 122°–24° C.

EXAMPLE 4

3-Chloro-4-hydroxynitrostyrene

3-Chloro-4-hydroxybenzaldehyde (15.6 g) and n-butylamine (9.12 g.) were refluxed in dry benzene (100 ml.) using Dean-Stark water separator for 3 hours. Benzene phase was concentrated. The oily aldimine (21 g.), nitromethane (21 ml.) and glacial acetic acid (63 ml.) were refluxed for 45 minutes. The crude product was obtained by adding the reaction mixture to ice-water. The title product was obtained by crystallising the crude product. The title product melted at 127°–29° C.

EXAMPLE 5

β-Methyl-3-chloro-4-hydroxynitrostyrene

3-Chloro-4-hydroxybenzaldehyde (15.6 g.) and n-butylamine (9.12 g.) were refluxed in dry benzene (150 ml.) at 100° C, by azeotropically distilling off the water of reaction. Benzene phase was concentrated to get the oily aldimine. The aldimine (21 g), nitroethane (21 ml.) and formic acid (65 ml.) were refluxed for 1 hour. The reaction mixture was diluted with ice-water. The crude product thus obtained was crystallised from aqueous ethanol to get the title product melting at 91°–93° C.

EXAMPLE 6

5-Chloro-2-hydroxynitrostyrene

5-Chloro-2-hydroxybenzaldehyde (15.6 g.) and n-butylamine (9.12 g) were refluxed in dry benzene (125 ml.) using Dean-Stark water separator for 3 hours. The benzene phase was concentrated to get the oily intermediate (23 g.). It was refluxed in glacial acetic acid (70 ml.) along with nitromethane (23 ml.) for 1 hour. The crude product was obtained by adding ice-water into the reaction mixture. The crude product was crystallised from benzene. The title product melted at 163–5° C.

EXAMPLE 7

β-Methyl-5-chloro-2-hydroxynitrostyrene

5-Chloro-2-hydroxybenzaldehyde (15.6 g.) and n-butylamine (9.12 g.) were refluxed in dry benzene (100 ml.) using Dean-Stark water separator for 3 hours. The benzene phase was concentrated. The crude aldimine (23 g.), nitroethane (23 ml.) and glacial acetic acid were refluxed for 1 hour. The reaction mixture was diluted with ice-water to get the oily final product. The oily product was twice crystallised from ethanol to get the title product; m.p. 104–6° C.

EXAMPLE 8

5-Bromo-2-hydroxynitrostyrene

5-Bromo-2-hydroxybenzaldehyde (20.1 g.) and n-propylamine (7.6 g.) were refluxed in dry benzene (125 ml.) using Dean-Stark water separator for 3.5 hours. The benzene phase was concentrated to get the oily aldimine. The aldimine (25 g.), nitromethane (25 ml.) and glacial acetic acid (75 ml.) were refluxed for 1 hour. The reaction mixture was poured into crushed ice to get the crude product. The crude product was first crystallised from aqueous ethanol and then from benzene-hexane to get the title product melting at 165–67° C.

EXAMPLE 9

β-Methyl-5-bromo-2-hydroxynitrostyrene

5-Bromo-2-hydroxybenzaldehyde (20.1 g.) and n-butylamine (9.12 g.) were refluxed in dry benzene (100 ml.) using Dean-Stark water separator for 3 hours. The benzene phase was concentrated. The crude aldimine (25 g.), nitroethane (25 ml.) and glacial acetic acid (75 ml.) were refluxed for 1 hour. The reaction mixture was diluted with ice-water to get the crude product which was crystallised from hexane to get the title product; m.p. 95–7° C.

Following the above procedure, the following compounds have also been prepared:

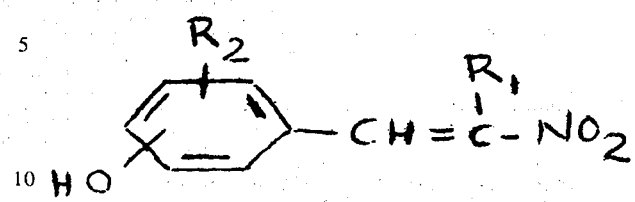

| $R_1$ | $R_2$ | CE (position) |
|---|---|---|
| H | H | 3 |
| $CH_3$ | H | 4 |
| $CH_3$ | H | 3 |
| $C_2H_5$ | H | 3 |
| $C_2H_5$ | H | 4 |
| $CH_3$ | H | 2 |
| $C_2H_5$ | H | 2 |
| H | H | 2 |
| H | Cl(Br) | 3(2) |
| $CH_3$ | Cl(Br) | 3(2) |
| $C_2H_5$ | Cl(Br) | 3(2) |
| H | Cl(Br) | 4 |
| $CH_3$ | Cl(Br) | 4 |
| $C_2H_5$ | Cl(Br) | 4 |

EXAMPLE 10

(O-p-Toluidinocarbonyl)-β-methyl-3-hydroxynitrostyrene

β-Methyl-3-hydroxynitrostyrene (1.79 g.) prepared according to the procedure of Example 1 and p-tolylisocyanate (1.33 g) were stirred in dry benzene (50 ml.) at room temperature. To the stirring mixture was added triethylamine (0.5 g.) and the mixture was heated at 80° C. for 4 hours. The reaction mixture was cooled. The crude product was filtered off and was crystallised from benzene – hexane to get the title product; m.p. 103–5° C.

EXAMPLE 11

(O-p-Bromoanilinocarbonyl)-β-methyl-3-hydroxynitrostyrene

β-Methyl-3-hydroxynitrostyrene (1.79 g.) prepared according to the procedure of Example 1 and p-bromophenylisocyanate (1.98 g.) were stirred in dry benzene (50 ml.) at room temperature. To the stirred mixture was added triethylamine (0.5 g.) and the mixture was kept at room temperature. The separated product was filtered off and was crystallised from benzene to get the title product melting at 152–4° C.

EXAMPLE 12

(O-Anilinocarbonyl)-3-chloro-4-hydroxynitrostyrene

3-Chloro-4-hydroxynitrostyrene (1.9 g.) prepared according to the procedure of Example 4 and phenylisocyanate (1.19 g.) were stirred in dry benzene (50 ml.) at room temperature and to the mixture was added triethylamine (0.5 g.). The mixture was stirred and was heated at 80° C for 4 hours. The reaction mixture was cooled. The solid product, which separated, was filtered off. It was crystallised from benzene to get the title product: m.p. 140–2° C(d).

EXAMPLE 13

(O-Cyclohexylaminocarbonyl)-3-chloro-4-hydroxynitrostyrene

3-Chloro-4-hydroxynitrostyrene (1.9 g.) prepared according to the procedure of Example 4 and cyclohexylisocyanate (1.25 g.) were stirred at room temperature in dry benzene (50 ml.). To the mixture was added triethylamine (0.5 g.) and the stirring continued at 80° C for 4 hours. The reaction mixture was cooled. The product was filtered off and was crystallised from benzene: m.p. 135–7° C(d).

EXAMPLE 14

(O-Anilinocarbonyl)-β-methyl-3-chloro-4-hydroxynitrostyrene

β-Methyl-3-chloro-4-hydroxynitrostyrene (1.94 g.) prepared according to the procedure of Example 5 and phenylisocyanate (1.19 g.) were stirred at room temperature in dry benzene (50 ml.). To the mixture was added triethylamine (0.5 g.) and the stirring continued at 80° C for 4 hours. On concentration, the reaction mixture yielded a residue which was crystallised from benzene - hexane to get the title product; m.p. 105–7° C.

EXAMPLE 15

(O-p-Toluidinocarbonyl)-β-methyl-3-chloro-4-hydroxynitrostyrene

β-Methyl-3-chloro-4-hydroxynitrostyrene (1.94 g) prepared according to the procedure of Example 5 and p-tolylisocyanate (1.33 g.) were stirred in dry benzene at room temperature. To the mixture was added triethylamine (0.5 g.) and the stirring continued at 80° C for 4 hours. The reaction mixture was concentrated and the residue was crystallised from benzene-hexane to get the title product melting at 100–2° C.

EXAMPLE 16

(O-p-Bromoanilinocarbonyl)-β-methyl-3-chloro-4-hydroxynitrostyrene

β-Methyl-3-chloro-4-hydroxynitrostyrene (1.94 g.) prepared according to the procedure of Example 5 and p-bromophenylisocyanate (1.98 g.) were stirred at room temperature in dry benzene (50 ml.). To the mixture was added triethylamine (0.5 g.) and stirring continued at 80° C for 4 hours. The reaction mixture was concentrated and the residue was crystallised from benzene - hexane. The title product thus obtained melted at 130–2° C.

EXAMPLE 17

(O-n-Butylaminocarbonyl)-β-methyl-3-chloro-4-hydroxynitrostyrene

β-Methyl-3-chloro-4-hydroxynitrostyrene (1.94 g.) prepared according to the procedure of Example 5 and n-butylisocyanate (0.99 g.) were stirred in dry benzene (50 ml.) at room temperature. To the stirred mixture was added triethylamine (0.5 g.) and stirring continued at 60° C. The reaction mixture was concentrated and the residue was crystallised from benzene - hexane. The title product melted at 130–2° C.

EXAMPLE 18

(O-n-Butylaminocarbonyl)-3-bromo-4-hydroxynitrostyrene

3-Bromo-4-hydroxynitrostyrene (2.44 g.) prepared according to the procedure of Example 2 and n-butylisocyanate (0.99 g.) were stirred at room temperature in dry benzene (50 ml.). To the mixture was added triethylamine (0.5 g.) and stirring continued at 80° C for 4 hours. The reaction mixture was cooled and the separated product was filtered off. It was crystallised from benzene to get the pure title product which melted at 103–5° C.

EXAMPLE 19

(O-p-Toluidinocarbonyl)-3-bromo-4-hydroxynitrostyrene

3-Bromo-4-hydroxynitrostyrene (2.44 g.) prepared according to the procedure of Example 2 and p-tolylisocyanate (1.33 g.) were stirred at room temperature in dry benzene (50 ml.). To the mixture was added triethylamine (0.5 g.) and stirring continued at 80° C for 4 hours. On cooling the reaction mixture, the product was separated. It was filtered off and was crystallised from benzene to get the title product; m.p. 157–60° C (d).

EXAMPLE 20

(O-p-Chloroanilinothiocarbonyl)-4-hydroxynitrostyrene

4-Hydroxynitrostyrene (1.65 g.) and p-chlorophenylisothiocyanate (1.69 g.) were stirred in dry benzene (50 ml.) at room temperature. To the mixture was added triethylamine (0.5 g.) and the stirring continued at 80° C for 4 hours. The reaction mixture was filtered hot. The product was suspended in hexane. The title product melted at 170–72° C with decomposition.

EXAMPLE 21

(O-Anilinothiocarbonyl)-4-hydroxynitrostyrene

4-Hydroxynitrostyrene (3.3 g.) and phenylisothiocyanate (2.7 g.) were stirred in dry benzene (100 ml.) at room temperature. To the mixture was added triethylamine (1 g.) and the stirring continued for 4 hours at 80° C. The reaction mixture was filtered hot. The product was suspended in hexane. The title product melted at 172–4° C (d).

EXAMPLE 22

(O-Cyclohexylaminothiocarbonyl)-β-methyl-4-hydroxynitrostyrene (O-p-Toluidinothiocarbonyl)-

β-Methyl-4-hydroxynitrostyrene (3.58 g.) prepared according to the process of the invention and cyclohexylisothiocyanate (2.8 g.) were stirred in dry benzene (100 ml.) at room temperature. To the mixture was added triethylamine (1 ml.) and the stirring continued at 80° C for 4 hours. On cooling the reaction mixture, the crude product was separated and was crystallised from benzene to get the title product: m.p. 115–17° C.

EXAMPLE 23

(0-p-Toluidinothiocarbonyl)-3-hydroxynitrostyrene

3-Hydroxynitrostyrene (3.3 g.) prepared according to the process of the invention and p-tolylisothiocyanate (2.98 g.) were stirred in dry benzene (100 ml.) at room temperature. To the mixture was added triethylamine (1 ml.) and the stirring continued at 80° C for 5 hours. The reaction mixture was concentrated and the residue was crystallised from benezen to get the title product; m.p. 160° C. (d)

EXAMPLE 24

(O-Anilinocarbonyl)-4-hydroxynitrostyrene

4-Hydroxynitrostyrene (1.65 g.) and phenyl isocyanate (1.19 g) were stirred in dry benzene (75 ml.) at room temperature. To the stirred mixture was added triethylamine (0.5 ml.) and the stirring continued for 4 hours at room temperature. The prduct was filtered off and was crystallised from benzene. The title product melted at 158–60° C.

EXAMPLE 25

(O-Cyclohexylaminocrbonyl)-4-hydroxynitrostyrene

4-Hydroxynitrostyrene (1.65 g.) and cyclohexylisocyanate (1.25 g.) were stirred in dry benzene (50 ml.) at room temperature. To the stirred mixture was added triethylamine (0.5 ml.) and the stirring continued for 4 hours at 80° C. The reaction mixture was cooled and the crude product was filtered off. The crude title product thus obtained was purified by crystallization from benzene: m.p. 175–77° C.

EXAMPLE 26

(O-p-Toluidinocarbonyl)-4-hydroxynitrostyrene

4-Hydroxynitrostyrene (3.3 g.) and p-tolylisocyanate (2.66 g.) were stirred in dry benzene (100 ml.) at room temperature. To the stirred mixture was added triethylamine (1 ml.) and the stirring continued for 4 hours at room temperature. The crude product was filtered off and was crystallised from benzene. The title product melted at 158° C (d).

EXAMPLE 27

(O-p-Bromoanilinocarbonyl)-4-hydroxynitrostyrene

4-Hydroxynitrostyrene (1.65 g.) and p-bromophenylisocyanate (1.98 g.) were stirred in dry benzene (75 ml.) at room temperature. To the stirred mixture was added triethylamine (0.5 ml.) and the stirring continued for 4 hours at room temperature. The product was filtered off and was crystallised from benzene to get the pure title product melting with decomposition at 210° C.

EXAMPLE 28

(O-Cyclohexylaminocarbonyl)-β-methyl-4-hydroxynitrostyrene

β-Methyl-4-hydroxynitrostyrene (1.79 g.) prepared according to the process of the invention and cyclohexylisocyanate (1.25 g.) were stirred in dry benzene (50 ml.) at room temperature. To the stirred mixture was added pyridine (0.5 ml.) and the stirring continued for 4 hours at 65° C. The reaction mixture was concentrated and the crude solid product was crystallised from benzene-hexane to get pure title product: m.p. 148–50° C.

EXAMPLE 29

(O-Anilinocarbonyl)-3-hydroxynitrostyrene

3-Hydroxynitrostyrene (1.65 g.) prepared according to the process of the invention and phenylisocyanate (1.19 g.) were stirred in dry toluene (50 ml.) at room temperature. To the stirred mixture was added thiethylamine (0.5 ml.) and the stirring continued for 4 hours, at 90° C. The reaction mixture was cooled and the crude product was filtered off. The title product was obtained after crystallising the crude product from benzene. The title product melted at 187–9° C with decomposition.

EXAMPLE 30

(O-p-Toluidinocarbonyl)-3-hydroxynitrostyrene

3-Hydroxynitrostyrene (1.65 g.) prepared according to the process of the invention and p-tolylisocyanate (1.33 g.) were stirred in dry toluene (50 ml) at room temperature. To the stirred mixture was added triethylamine (0.5 ml.) and the stirring continued for 4 hours at 90° C. The reaction mixture was cooled. The crude product was filtered off and was crystallised to get the pure title product; m.p. 218–20° C (d).

EXAMPLE 31

(O-p-Bromoanilinocarbonyl)-3-hydroxynitrostyrene

3-Hydroxynitrostyrene (1.65 g.) prepared according to the process of the invention and p-bromophenylisocyanate (1.98 g.) were stirred in dry toluene (50 ml.) at room temperature. To the stirred mixture was added triethylamine (0.5 ml.) and the stirring continued for 4 hours at room temperature. The crude product was filtered off and was crystallised from benzene to get the pure title product melting at 158–60° C.

EXAMPLE 32

(O-n-Butylaminocarbonyl)-3-hydroxynitrostyrene

3-Hydroxynitrostyrene (1.65 g.) prepared according to the process of the invention and n-butylisocyanate (0.99 g.) were stirred in dry toluene (50 ml.) at room temperature. To the stirred mixture was added triethylamine (0.5 ml.) and stirring continued for 4 hours, at 85° C. The reaction mixture was concentrated. The oily residue was crystallised from hexane to get pure title product: m.p. 80°–2° C.

EXAMPLE 33

β-Methyl-[4-(5-nitrothiazol-2-yl)-oxy]-nitrostyrene

β-Methyl-4-hydroxynitrostyrene (5.37 g.) prepared according to the process of the invention and sodium ethoxide (2.04 g.) were stirred in ethanol (20 ml.) at room temperature for 1 hour. The solvent was removed at 40°–45° C under reduced pressure and the residue was suspended in solvent ether and filtered to get the sodium salt of β-methyl-4-hydroxynitrostyrene (5.2 g.) 2-Chloro-5-nitrothiazole (4.28 g) and the sodium salt of β-methyl-4-hydroxynitrostyrene (5.2 g. were mixed in DMSO (Dimethysulfoxide) (10 ml.) under cooling. The mixture was warmed at 50°–55° C for 2 hours. The reaction mixture was diluted with cold water and the separated product was suspended in ethanol. The crude product was crystallised from benzene-hexane: m.p. 102°–3° C.

EXAMPLE 34

[4-(5-Nitrothiazol-2-yl)-oxy]-nitrostyrene

4Hydroxynitrostyrene (3.3 g.) and anhydrous potassium carbonate (2.76 g.) were stirred at room temperature in dry acetone (30 ml.) for 3 hours. To the reaction mixture was added 2-chloro-5-nitrothiazole (3.3 g.) and the stirring continued at room temperature for 3 hours. After keeping the reaction mixture overnight at room temperature, it was diluted with water (150 ml.). The product was filtered off and was suspended in 1% NaOH sol. (30 ml.) followed by 3% CH₃COOH (50 ml.). The crude product was crystallised from benzene-hexane; m.p. 152°–4° C.

Following the above procedure the following compounds have been prepared.

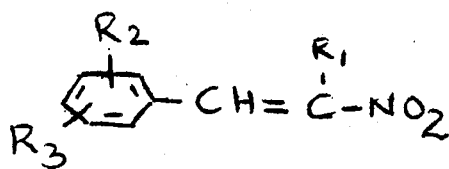

1. A compound of the formula

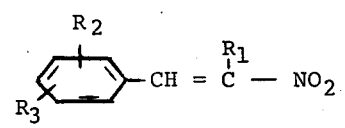

wherein $R_1$ is selected from the group consisting of H, $CH_3$ and $C_2H_5$, $R_2$ is selected from the group consisting of H, Cl and Br, and $R_3$ is 5-nitrothiazol-2-yl-oxy.

2. A compound as claimed in claim 1, wherein $R_1$ is $CH_3$.

3. A compound as claimed in claim 1, wherein said compound is β-methyl-[4-(5-nitrothiazol-2-yl)-oxo]-nitrostyrene.

4. A compound as claimed in claim 1, wherein said compound is [4-(5-nitrothiazol-2-yl)-oxy]-nitrostyrene.

| $R_1$ | $R_2$ | $R_3$(Position) | |
|---|---|---|---|
| H(CH₃) (Et) | H(Cl)(Br) | C₆H₅—NH—CO—O | (2,3 or 4) |
| " | " | CH₃–⌬–NHCO—O | " |
| " | " | OCH₃–⌬–NHCO—O | " |
| " | " | CR–⌬–NH.CO—O | " |
| " | " | NO₂–⌬–NH—CO—O | " |
| " | " | CH₃NH—CO—O | " |
| " | " | C₂H₅—NHCO—O | " |
| " | " | C₃H₇NH—CO—O | " |
| " | " | C₄H₉—NHCO—O | " |
| " | " | C₆H₁₁—NH—CO—O | |

Having ascertained the invention and the manner in which the same is to be performed, what is claimed is: